United States Patent
Ishii et al.

(10) Patent No.: US 9,827,538 B2
(45) Date of Patent: Nov. 28, 2017

(54) APPARATUS FOR PRODUCING MIXED SOLUTION AND METHOD FOR PREPARING MIXED SOLUTION

(71) Applicant: Asahi Kasei Chemicals Corporation, Tokyo (JP)

(72) Inventors: Yusuke Ishii, Tokyo (JP); Takaaki Kato, Tokyo (JP)

(73) Assignee: ASAHI KASEI CHEMICALS CORPORATION, Tokyo (JP)

(*) Notice: Subject to any disclaimer, the term of this patent is extended or adjusted under 35 U.S.C. 154(b) by 0 days.

(21) Appl. No.: 15/225,626

(22) Filed: Aug. 1, 2016

(65) Prior Publication Data
US 2016/0340295 A1 Nov. 24, 2016

Related U.S. Application Data

(62) Division of application No. 13/980,220, filed as application No. PCT/JP2012/052122 on Jan. 31, 2012.

(30) Foreign Application Priority Data

Jan. 31, 2011 (JP) .................................. 2011-017937

(51) Int. Cl.
| | |
|---|---|
| *B01F 15/00* | (2006.01) |
| *B01F 1/00* | (2006.01) |
| *B01J 19/02* | (2006.01) |
| *B01J 19/18* | (2006.01) |
| *C07C 51/41* | (2006.01) |
| *B01J 31/22* | (2006.01) |

(Continued)

(52) U.S. Cl.
CPC .......... *B01F 1/0011* (2013.01); *B01F 1/0016* (2013.01); *B01F 15/0022* (2013.01);
(Continued)

(58) Field of Classification Search
CPC ...... C07C 253/00; C07C 253/24; B01J 37/04; B01F 15/06; B01F 15/00831; B01F 15/0022
See application file for complete search history.

(56) References Cited

U.S. PATENT DOCUMENTS

| | | | | |
|---|---|---|---|---|
| 3,433,823 A | * | 3/1969 | McMahon | ............. B01J 27/198 502/204 |
| 4,415,752 A | * | 11/1983 | Decker | .................. B01J 23/002 502/241 |

(Continued)

FOREIGN PATENT DOCUMENTS

| | | |
|---|---|---|
| CN | 201305286 Y | 9/2009 |
| EP | 0 895 809 A1 | 2/1999 |

(Continued)

OTHER PUBLICATIONS

European Search Report, dated Jan. 7, 2014, for Patent Application No. 12741952.1.

(Continued)

*Primary Examiner* — Tony G Soohoo
*Assistant Examiner* — Anshu Bhatia
(74) *Attorney, Agent, or Firm* — Birch, Stewart, Kolasch & Birch, LLP (57) ABSTRACT

An apparatus for producing a mixed solution, comprising a mixing vessel for preparing an aqueous mixed solution containing a dicarboxylic acid and an Nb compound and a filter for the aqueous mixed solution connected to the mixing vessel via a pipe, the mixing vessel being anticorrosive and equipped with a stirring unit, a heating unit and a cooling unit for the aqueous mixed solution, wherein the aqueous mixed solution prepared in the mixing vessel is fed to the filter via the pipe and filtered in the filter under increased pressure.

9 Claims, 1 Drawing Sheet

(51) Int. Cl.
*C07C 253/24* (2006.01)
*B01J 23/28* (2006.01)
*B01J 37/00* (2006.01)
*B01F 15/06* (2006.01)
*B01J 37/04* (2006.01)

(52) U.S. Cl.
CPC ........ *B01F 15/00831* (2013.01); *B01F 15/06* (2013.01); *B01J 19/02* (2013.01); *B01J 19/1862* (2013.01); *B01J 23/28* (2013.01); *B01J 31/2239* (2013.01); *B01J 37/009* (2013.01); *B01J 37/0045* (2013.01); *B01J 37/04* (2013.01); *C07C 51/412* (2013.01); *C07C 253/24* (2013.01); *B01F 2015/061* (2013.01); *B01F 2015/062* (2013.01); *B01F 2215/0036* (2013.01); *B01J 2219/00094* (2013.01); *B01J 2219/00162* (2013.01); *B01J 2219/0209* (2013.01); *B01J 2219/0245* (2013.01); *B01J 2231/70* (2013.01); *B01J 2523/00* (2013.01); *B01J 2531/57* (2013.01); *Y02P 20/52* (2015.11)

(56) References Cited

U.S. PATENT DOCUMENTS

| | | | |
|---|---|---|---|
| 5,808,148 A | 9/1998 | Gogate et al. | |
| 6,036,880 A | 3/2000 | Komada et al. | |
| 6,048,396 A * | 4/2000 | Yanagisawa | C30B 7/00 117/71 |
| 6,494,608 B1 | 12/2002 | Retamal et al. | |
| 6,923,567 B2 | 8/2005 | Bibbo et al. | |
| 7,754,910 B2 | 7/2010 | Lugmair et al. | |
| 2003/0017944 A1 | 1/2003 | Hinago et al. | |
| 2008/0073810 A1 | 3/2008 | Ito et al. | |
| 2008/0200715 A1 | 8/2008 | Lugmair et al. | |
| 2010/0149908 A1 | 6/2010 | Singh et al. | |
| 2013/0001174 A1 | 1/2013 | Zacharias et al. | |

FOREIGN PATENT DOCUMENTS

| | | |
|---|---|---|
| EP | 2540383 A1 | 1/2013 |
| GB | 2 034 190 A | 6/1980 |
| JP | 11-47598 A | 2/1999 |
| JP | 11-253801 A | 9/1999 |
| JP | 2002-159853 A | 6/2002 |
| JP | 2007-203478 A | 8/2007 |
| JP | 2010-519202 A | 6/2010 |

OTHER PUBLICATIONS

International Search Report, dated Apr. 10, 2012, issued in PCT/JP2012/052122.
Written Opinion of the International Searching Authority, dated Apr. 10, 2012, issued in PCT/JP2012/052122.

* cited by examiner

APPARATUS FOR PRODUCING MIXED SOLUTION AND METHOD FOR PREPARING MIXED SOLUTION

CROSS-REFERENCE TO RELATED APPLICATIONS

This application is a Divisional of co-pending application Ser. No. 13/980,220 filed on Jul. 17, 2013, which is a National Phase of PCT International Application No. PCT/JP2012/052122 filed on Jan. 31, 2012, which claims priority under 35 U.S.C. §119(a) to Patent Application No. 2011-017937 filed in Japan on Jan. 31, 2011. All of the above applications are hereby expressly incorporated by reference into the present application.

FIELD OF THE INVENTION

The present invention relates to an apparatus for producing a mixed solution containing a dicarboxylic acid and an Nb compound, and a method for preparing the mixed solution.

DESCRIPTION OF THE RELATED ART

Conventionally, the composite metal oxides containing several metals such as molybdenum and vanadium are used as the catalyst for producing unsaturated nitrile production. For the composition of the composite metal oxides, the metal type and ratio have been aggressively studied to pursue further improvement of the catalyst properties.

To produce the composite metal oxide catalyst, a slurry containing a metal salt composing the catalyst is prepared, spray dried and calcined. In this step, if the metal salt-containing slurry is not in a uniform state, the catalyst to be obtained is also ununiformed, hence failing to provide a composite metal oxide having the composition optimized as a result of the extensive studies as described above. Thus, it is desired to prepare a slurry wherein a metal salt is uniformly dissolved, however, some metal species that are mixed form a hardly soluble salt, which needs to be thoroughly dissolved.

To dissolve a hardly soluble metal species, a method is known wherein various acids, bases and chelate compounds are added and heated. In particular, elements such as niobium, tantalum, and the like, are known to be hardly soluble which makes it difficult to prepare a uniform solution. For example, Patent Literatures 1 and 2 describe a method for preparing an aqueous Nb solution by adding a dicarboxylic acid such as an oxalic acid, to dissolve the Nb compound for the preparation of a composite metal oxide.

CITATION LIST

Patent Literature

[Patent Literature 1] Japanese Patent Laid-Open No. H11-253801
[Patent Literature 2] Japanese Patent Laid-Open No. H11-047598

Technical Problem

Patent Literatures 1 and 2 describe the optimal dicarboxylic acid and Nb compound ratio at the time of preparing the catalyst for producing acrylonitrile from propane. However, when a dicarboxylic acid is added in the ratio as described in these literatures to prepare a niobium solution, problems are posed in that an NB compound dissolved in a laboratory scale partially remains undissolved up in the industrial scale, a dicarboxylic acid is deposited in the middle of a pipe or a niobium solution wherein a dicarboxylic acid is dissolved in a larger amount than an intended amount is obtained.

In view of the above circumstances, an object of the present invention is to provide an apparatus for producing a mixed solution and a method for preparing a mixed solution by which an Nb compound remained undissolved or deposited is reduced and a high niobium yield and productivity are achieved.

SUMMARY OF THE INVENTION

The present inventors have conducted extensive studies to solve the above problems and found that an undissolved or deposited Nb compound is reduced and the Nb yield and the mixed solution productivity are enhanced by using a production apparatus provided with an anticorrosive mixing vessel equipped with a stirring unit, a heating unit and a cooling unit and a filter for filtering an undissolved Nb compound and a deposited dicarboxylic acid while applying a pressure in the filtering step, and thereby accomplished the present invention.

More specifically, the present invention is as follows.

[1]
An apparatus for producing a mixed solution, comprising:
a mixing vessel for preparing an aqueous mixed solution containing a dicarboxylic acid and a Nb compound and;
a filter for the aqueous mixed solution connected to the mixing vessel via a pipe,
the mixing vessel being anticorrosive and equipped with a stirring unit, a heating unit and a cooling unit for the aqueous mixed solution, wherein the aqueous mixed solution prepared in the mixing vessel is fed to the filter via the pipe and filtered in the filter under an increased pressure.

[2]
The apparatus for producing the mixed solution according to the above [1], wherein a jacket is disposed outside the filter and a heating medium and/or a cooling medium is fed into the jacket to adjust a temperature of the filter.

[3]
The apparatus for producing the mixed solution according to the above [1] or [2], wherein a jacket is disposed outside the mixing vessel and the jacket serves as the heating unit when a heating medium is fed thereinto and serves as the cooling unit when a cooling medium is fed thereinto.

[4]
The apparatus for producing the mixed solution according to any one of the above [1] to [3], wherein the mixing vessel is made of a glass and/or a fluoro-based resin or has an inner surface coated with a glass and/or a fluoro-based resin.

[5]
The apparatus for producing the mixed solution according to any one of the above [1] to [4], wherein a container for storing a filtrate is connected to the filter and is equipped with a concentration measuring unit and a concentration adjusting unit for the filtrate.

[6]
The apparatus for producing the mixed solution according to any of the above [1] to [5], wherein the mixing vessel is equipped with a pressure adjusting unit and a pressure in the mixing vessel is adjusted by the pressure adjusting unit.

[7]
A method for preparing a mixed solution comprising the steps of:

heating and stirring a dicarboxylic acid, an Nb compound and water in an anticorrosive mixing vessel so as to obtain an aqueous mixed solution;

cooling and stirring the aqueous mixed solution and;

feeding the aqueous mixed solution into a filter to filter under an increased pressure.

[8]

The method for preparing the mixed solution according to the above [7], wherein a temperature of the aqueous mixed solution is adjusted in the filtration step.

[9]

The method for preparing the mixed solution according to the above [7] or [8], wherein, in the step of heating and stirring the dicarboxylic acid, the Nb compound and the water in an anticorrosive mixing vessel to obtain the aqueous mixed solution, a niobium and a dicarboxylic acid are dissolved in the aqueous mixed solution.

[10]

The method for preparing the mixed solution according to any of the above [7] to [9], wherein in the step of cooling and stirring the aqueous mixed solution, a dicarboxylic acid is deposited from the aqueous mixed solution.

[11]

The method for preparing the mixed solution according to any of the above [7] to [10], further comprising the steps of:

measuring a concentration of the obtained filtrate after the filtration step and adding a dicarboxylic acid and/or water to the filtrate when a dicarboxylic acid/Nb molar ratio is not within a predetermined range.

[12]

The method for preparing the mixed solution according to the above [11], wherein the dicarboxylic acid/Nb molar ratio (=X) of the filtrate is adjusted to 1<X<4.

[13]

The method for preparing the mixed solution according to any of the above [7] to [12], wherein the dicarboxylic acid is an oxalic acid.

[14]

A method for preparing a Mo, V, Sb and Nb-containing catalyst comprising:

preparing a mixed solution according to any of the above [7] to [13] and;

using the mixed solution therefor.

[15]

A method for producing an unsaturated nitrile, wherein a catalyst is prepared by the method according to the above [13] and the obtained catalyst is caused to contact a propane or an isobutane, an ammonia and an oxygen.

Advantageous Effect of the Invention

According to the present invention, in the preparation of a mixed solution containing a dicarboxylic acid and an Nb compound, an undissolved or deposited Nb compound is reduced and the Nb yield and the mixed solution productivity can be enhanced.

DETAILED DESCRIPTION OF THE PREFERRED EMBODIMENTS

Hereinafter, the embodiments to carry out the present invention (hereinafter referred to as "the present embodiment") will be described in details. The present invention is not limited to the following embodiments, and can be carried out in various modifications within the spirit and scope of the invention.

Figure 1:
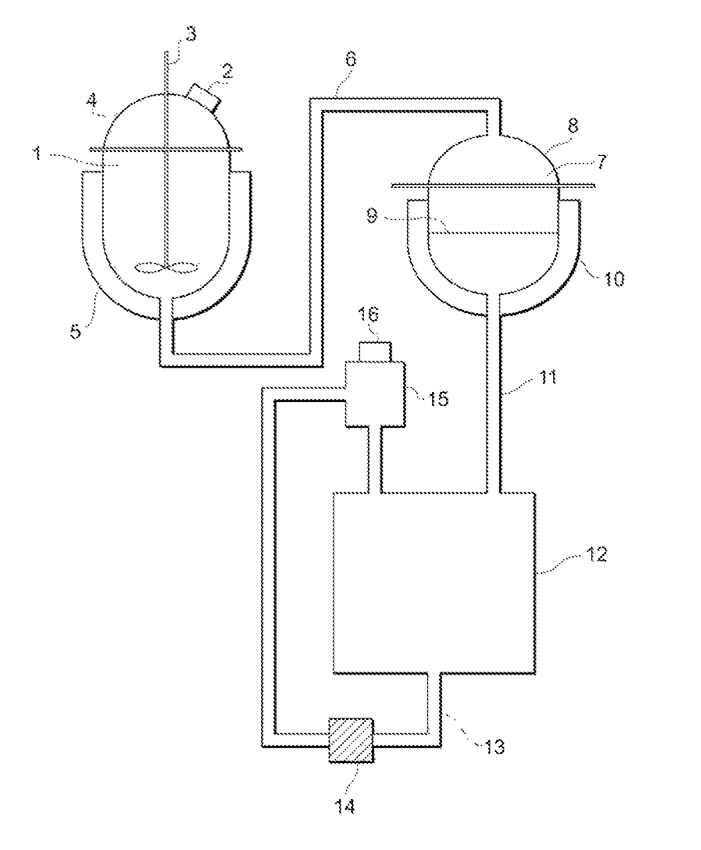
FIG. 1 shows an example of schematic views of an apparatus for producing a mixed solution according to the present embodiment.

In the FIGURE, the same elements are denoted by the same symbols, the description of which is omitted. The positional relation of the left, right, top and bottom is, unless otherwise stated, based on the positional relation as shown in the FIGURE. The scale of the apparatus and members is not limited to the scale shown in the FIGURE.

The apparatus for producing a mixed solution according to the present embodiment is an apparatus for producing a mixed solution, comprising a mixing vessel for preparing an aqueous mixed solution containing a dicarboxylic acid and an Nb compound and a filter for the aqueous mixed solution connected to the mixing vessel via a pipe, the mixing vessel being anticorrosive and equipped with a stirring unit, a heating unit and a cooling unit for the aqueous mixed solution, wherein the aqueous mixed solution prepared in the mixing vessel is fed to the filter via the pipe and filtered in the filter under increased pressure.

FIG. 1 shows an example of the schematic views of the apparatus for producing a mixed solution according to the present embodiment.

The apparatus for producing a mixed solution according to the present embodiment has an anticorrosive mixing vessel. The mixing vessel 1 shown in FIG. 1 is equipped with an inlet 2, stirring impellers 3, a mixing vessel hood 4 and a jacket 5. The mixing vessel contacts an aqueous mixed solution containing a dicarboxylic acid and an Nb compound but, owing to the anticorrosive properties, is hard to be eroded and can be stably used. In the present embodiment, the "anticorrosive" is defined as the corrosion rate being 0.2 mm/year or less when the aqueous mixed solution is maintained at 40° C. in an acid solution under a condition of an oxalic acid concentration of 70 mol/(kg-solution).

Examples of the anticorrosive material include at least one selected from the group consisting of fluoro-based resins, glasses and silicone resins, and examples of the mixing vessel comprising an anticorrosive material include fluoro-based resin containers, glass containers, and the like. The mixing vessel used herein should only have the anticorrosive inner surface which contacts the aqueous mixed solution and may be made from a composite material of a non-anticorrosive material and an anticorrosive material, and specific examples include a metal mixing vessel with a fluoro-based resin and/or a glass container fitted inside. In particular, the mixing vessel having the inner surface treated with a coating such as glass lining (the glass coating treatment to a metal product) can be made into a complex shape and easily produced into a large volume container, hence preferable.

The apparatus for producing a mixed solution according to the present embodiment is equipped with a mixing vessel and a filter for the aqueous mixed solution connected to the mixing vessel via a pipe, and the mixing vessel is provided with a stirring unit, a heating unit and a cooling unit for the aqueous mixed solution. The mixing vessel 1 shown in FIG. 1 is connected via a pipe 6 to a filter 7 engaged with a filter hood 8, and the filter 7 has a filter paper 9 arranged inside so that an outlet at the bottom is covered. The filter 7 has a jacket 10 so that the filter 7 is heated, cooled or maintained at a certain temperature while the mixed solution is passing through the filter paper. The jacket 10 is a device serving as both a heating unit and a cooling unit which serves as a heating unit when a heating medium is fed and serves as a cooling unit when a cooling medium is fed. The heating unit and/or the cooling unit shown in FIG. 1 is a jacket disposed outside the mixing vessel, but the heating unit and/or the cooling unit may be a coil positioned outside and/or inside the mixing vessel. Since such a coil does not inhibit the stirring of the aqueous mixed solution or is free from the adhesion of the mixed solution, it is preferably disposed outside the mixing vessel. When a coil is disposed inside the mixing vessel, the coil is preferably composed of an anticorrosive material or the outer surface of the coil is preferably coated with an anticorrosive material. The heating medium is not limited and steam, hot water, and the like, can be used, and the cooling medium is also not limited and water, alcohol, and the like, can be used.

A stirring unit for the aqueous mixed solution is provided in the mixing vessel. The method for stirring and the shape of the stirring unit are not limited but those capable of exhibiting the desirable stirring power to be described later are preferable. In addition to multistage impellers, anchor impellers, helical axial impellers, helical ribbon impellers, examples of the stirring unit include stirring blades for a low viscous solution such as propellers, disc turbins, fan turbins, curved blade fan turbines, feather blade turbines, and inclined blade turbines. The mixing vessel may be equipped with an ultrasonic vibration device. Application of ultrasonic vibrations together with the stirring is expected to contribute to the dissolution of an Nb compound. However, when the mixing vessel is made of glass or treated with a glass lining, the vibration affects the vessel likely causing a crack, and hence is preferably made of a resin when an ultrasonic vibration device is used.

The stirring unit directly contacts the aqueous mixed solution and is hence preferably anticorrosive. Examples of the anticorrosive stirring unit include stirring impellers made of fluoro-based resin, stirring impellers coated with a fluoro-based resin, or the like, and stirring impellers treated with a glass lining, with the glass lined-stirring impellers being desirable.

The mixing vessel is preferably hooded for the purpose of preventing foreign matters from entering and maintaining the temperature of the aqueous mixed solution. The hood may be composed of the same material as the mixing vessel, however, when the hood is not immersed in the aqueous mixed solution, some metals having comparatively high anticorrosive properties such as SUS316, SUS316L, and Hastelloy C may be used, provided that those which are glass lined are preferably used. The hood preferably contacts the main body of the mixing vessel with no gap. When feeding a solid matter into the mixing vessel, the solid matter may be fed every time the hood is opened or fed by pneumatic conveying system from the pipe, however, when the hood of the main body is opened and closed, particles are deposited between the hood and the mixing vessel or when the aqueous mixed solution inside is heated, the steam is likely to leak out, thus the hood is preferably provided with a special inlet for feeding particles.

The hood may be equipped with a jacket as a heating unit and/or a cooling unit. When the mixing vessel is equipped with the hood, the inside the mixing vessel is a closed system and the internal pressure is sometimes applied or reduced at the time of heating or cooling the aqueous solution as to be described later, and for this reason, when the mixing vessel is made of glass or treated with a glass lining, the mixing vessel may break. To prevent such a breakage and maintain the pressure in the system, the mixing vessel is preferably equipped with a pressure adjusting unit capable of adjusting the pressure by introducing air into the mixing vessel. A pressure adjusting unit, for example, is provided with a pressure adjusting valve in the main body and a pipe for sending a compressed gas, e.g., air, nitrogen and oxygen into the system, to maintain a constant pressure inside the vessel main body.

The mixing vessel is connected to the filter via the pipe. The aqueous mixed solution is filtered by the filter under increased pressure from the viewpoint of the productivity. When the natural filtration is performed, the productivity of the filtrate is reduced and the yield of the solution is reduced, whereas when the filtration is performed under a reduced pressure, the temperature of the filtrate drops as a part of the filtrate is gasified and a solid matter is likely to deposit in the filtrate. Further, as the filtrate is gasified, the solution concentration is likely to change as the filtration time is extended. The "under increased pressure" indicates a state in which a pressure is applied so that a pressure higher than normal pressure is achieved, and the extent of the pressure applied is not limited but preferably 10 K/G or less, more preferably 5 K/G or less, further preferably 1 K/G or less. Even when a pressure exceeds 10 K/G, the filtration can be carried out without any problems but the productivity may be reduced because the residue is compacted causing the filtration to take longer time.

The filter material is not limited and membrane filters may be used in addition to filter papers. The shape of the filer may suitably be selected from those to which these filter materials can be applied. The size of the filter may suitably be selected in accordance with the amount, etc., of the mixed solution to be produced but, from the viewpoints of the productivity and the cost of apparatus, the ratio of filter diameter (mm)/aqueous mixed solution amount (kg) is preferably 0.5 to 3. The filter diameter (mm) and the mixed solution amount (kg) are, for example, 500 to 4000 mm, 0.2 to 8 t.

Depending on the concentration and temperature of the aqueous mixed solution passing through the filter, the filter is sometimes required to be highly anticorrosive but, when the temperature of the filtrate is about 10 to about 20° C., the filter may be composed of a metal that is comparatively anticorrosive. Example of the metal that is comparatively anticorrosive include SUS316, SUS316L, Hastelloy C, and the like, described earlier. Moreover, the filter may be equipped with a temperature adjusting unit. By way of the temperature adjusting unit provided to the filter, the temperature of the aqueous mixed solution to be filtered can be heated, cooled or maintained. Specific examples of the temperature adjusting unit include a jacket deposited outside the filter, a temperature controlling coil set inside the container, and the like. When a jacket is mounted outside the filter, a heating medium and/or cooling medium is fed into the jacket to regulate the temperature of the filter. Alternatively, the apparatus for producing a mixed solution may be placed in a room where the temperature is controlled to the same temperature as that at the time of the filtration.

The filter is connected to the mixing vessel via the pipe, which is also preferably composed of an anticorrosive material as in the mixing vessel. Preferred pipe material and embodiment are the same as in the mixing vessel. However, when the temperature of the aqueous mixed solution passing through the pipe is comparatively low, the pipe may be composed of metals comparatively anticorrosive such as SUS316, SUS316L, Hastelloy C, and the like.

Since the solid matters such as the Nb compound or a dicarboxylic acid produced and/or remained in the aqueous mixed solution may block the pipe, one or more pipes connecting the mixing vessel and the filter are preferably provided. The pipe preferably has an adequate diameter so that the solid matter deposited from the aqueous mixed solution does not cause the blockage. Specifically, the diameter is preferably 1 inch or more. The pipe is preferably connected to the bottom or lower part of the mixing vessel. The aqueous mixed solution can be fed from the mixing vessel to the filter using a pressure, a pump, etc.; however, considering the burden of corrosion on the pumping parts, the feeding using a pressure is desirable.

The pipe preferably has a unit for maintaining the temperature of the aqueous mixed solution passing therethrough. The corrosion of the pipe caused by a dicarboxylic acid and the solid matter deposited in the aqueous mixed solution and accumulated in the pipe can be prevented by preventing the temperature of the mixed solution from being increased and/or decreased while the aqueous mixed solution passes through the pipe. The pipe may be a trace pipe, a two-pipe system or wrapped with a heat insulating material so that the mixed solution in the pipe and the mixed solution in the mixing vessel have the same temperature. The trace pipe refers to a pipe through which a cooled or heated liquid passes and disposed along the pipe through which the mixed solution passes, and the trace pipe is typically arranged so that both contact each other. The arrangement of the trace pipe is not limited but the trace pipe is typically wrapped around the pipe through which the mixed solution passes at even intervals.

Further, a container is connected to the filter for storing the filtrate and may also be equipped with a concentration measuring unit and a concentration adjusting unit for the filtrate. The filter 7 shown in FIG. 1 is connected to a container 12 via a pipe 11. The container 12 may be any container capable of accommodating a liquid and the shape and size are not limited.

The filtrate obtained after passing through the filter is accommodated in a storage container (Y) via a container (X) connected to the downstream of the filter (the lower part of the filter paper 9 in the filter 7 shown in FIG. 1) but, from the viewpoint of flexible retention period, the storage container (Y) is preferably anticorrosive. It is preferred to arrange more than one container (Y) from the viewpoint of production efficiency. When adjusting the concentration of the mixed solution, the storage container (Y) is preferably linked to a pot (Z) composed of a corrosive material via a pipe. The container 12 shown in FIG. 1 is linked to a pot 15 via a pipe 13, which is equipped with a pump 14 for sending the solution. Further, the pot 15 is provided with a pot inlet 16. The dicarboxylic acid concentration and the niobium concentration in the filtrate in the storage container (Y) are measured using a concentration measuring unit, and when the concentration is insufficient, a required amount of the component that is short is housed in the pot (Z). The filtrate is introduced into the pot and is allowed to stand in a state in which a dicarboxylic acid and the filtrate contact with each other to dissolve the dicarboxylic acid and niobium, followed by returning the supernatant to the storage container (Y), whereby the mixed solution having an intended dicarboxylic acid concentration and/or niobium concentration can be obtained. The pot (Z) connected to the container (Y) herein serves as the concentration adjusting unit.

The concentration requirement in dicarboxylic acid and niobium does not have to be strict and, when the dicarboxylic acid/niobium ratio is emphasized, the pot (Z) preferably accommodates the dicarboxylic acid from the viewpoint of solubility. Thus, to achieve the predetermined dicarboxylic acid/niobium ratio, the cooling temperature in the mixing vessel and the filter is set slightly lower than the cooling temperature at which the predetermined dicarboxylic acid/niobium ratio is achieved, and, after reducing the amount of the dicarboxylic acid, the shortage is fed into the pot and mixed with the filtrate by which the dicarboxylic acid/niobium ratio is enabled to be maintained.

The method for preparing the mixed solution of the present embodiment comprises the steps of
heating and stirring a dicarboxylic acid, an Nb compound and water in an anticorrosive mixing vessel to obtain an aqueous mixed solution,
cooling and stirring the aqueous mixed solution, and
feeding the aqueous mixed solution to a filter and filtering under increased pressure.

In the method for preparing the mixed solution of the present embodiment, first, a dicarboxylic acid, an Nb compound and water are heated and stirred in an anticorrosive mixing vessel to obtain an aqueous mixed solution.

The Nb compound is not limited insofar as the compound contains niobium, but both are hardly soluble and hence dissolved in the presence of a dicarboxylic acid. Specific examples of the Nb compound include niobium hydrogen oxalate, ammonium niobium oxalate, $NbCl_3$, $NbCl_5$, $Nb_2(C_2O_4)_5$, $Nb_2O_5$, niobic acids, $Nb(OC_2H_5)_5$, niobium halides and niobium ammonium halide salts, with niobic acids and niobium hydrogen oxalate being preferable from the viewpoint of little affect to other metals when the aqueous mixed solution is mixed with other metals. The niobic acids encompass niobium hydroxides and niobium oxides. Since the Nb compound sometimes decomposes depending on long-term preservation and dehydration progress, it is preferred to use the fresh compound immediately after the production for the preparation of the aqueous mixed solution, but the compound somewhat decomposed may also be used.

The Nb compound may be a solid or a suspension before the mixed solution is prepared. When a niobic acid is used, the particle diameter is preferably small from the viewpoint of easy dissolution. The niobic acid can be washed in ammonia water and/or water before use.

Examples of the dicarboxylic acid include oxalic acid, malonic acid, succinic acid and glutaric acid, however, from the viewpoint of controlling the over-reduction of the metal oxide in the calcination stage at the time of producing a catalyst, oxalic anhydride and oxalic acid dihydrate are preferable. The dicarboxylic acid may be added singly or two or more dicarboxylic acids may be added in combination.

The concentration of niobium at the time of preparing the aqueous mixed solution is preferably 0.1 to 1 (mol-Nb/kg-solution), more preferably 0.1 to 0.9 (mol-Nb/kg-solution), further preferably 0.1 to 0.8 (mol-Nb/kg-solution). When a niobium concentration is below 0.1 (mol-Nb/kg-solution), a large amount of the niobium solution is required when feeding a required amount of niobium at the time of preparing a catalyst using this solution, consequently reducing the solid content in the catalyst raw material prepared solution, whereby the formability of the catalyst tends to be deteriorated. In contrast, when a niobium concentration exceeds 1 (mol-Nb/kg-solution), the hardly soluble Nb compound remains undissolved, likely making it difficult to filter and difficult to prepare the uniform mixed solution.

The concentration of the dicarboxylic acid at the time of preparing the aqueous mixed solution is preferably 0.2 to 5 (mol-Nb/kg-solution), more preferably 0.2 to 4.5 (mol-Nb/kg-solution), further preferably 0.2 to 4 (mol-Nb/kg-solution). When a dicarboxylic acid concentration is below 0.2 (mol-Nb/kg-solution), the hardly soluble Nb compound remains undissolved, likely making it difficult to filter and difficult to prepare the uniform mixed solution. In contrast, when a dicarboxylic acid concentration exceeds 5 (mol-Nb/kg-solution), an excess amount of the dicarboxylic acid crystal is deposited in the cooling step to be described later, likely making it difficult to filter and causing the pipe to be blocked. The molar ratio of the dicarboxylic acid/niobium at the time of preparing the aqueous mixed solution is preferably 3 to 6. When a molar ratio of the dicarboxylic acid/niobium exceeds 6, the solubility of the Nb compound is likely to increase and the niobium component is hardly deposited after cooling, enhancing the niobium yield, however, at the same time, the dicarboxylic acid is likely to be deposited in an increased amount, reducing the yield of the dicarboxylic acid. Conversely, when a molar ratio of the dicarboxylic acid/niobium is below 3, the insoluble Nb compound is likely to be increased, reducing the niobium yield.

Described below is an example of the method for preparing a dicarboxylic acid/Nb mixed solution using an apparatus having a filter provided with a jacket and an oxalic acid used as the dicarboxylic acid in the oxalic acid/niobium ratio of 1<oxalic acid/niobium<4 at a niobium concentration of 0.3 to 1.0 mol/L.

To adjust the hardly soluble niobium to a concentration of 0.3 mol/L or more, it is preferred that the oxalic acid/niobium ration be set greater than 1 and the temperatures at the time of preparation and/or filtration be set in consideration of a saturated concentration. To adjust the niobium concentration to 0.3 to 1.0 mol/L, depending on the concentration of the mixed solution, the oxalic acid and/or niobium is partially or wholly dissolved by raising the temperature to a higher concentration than the intended concentration and the temperature is subsequently cooled to the temperature at which a suitable saturated concentration is attained to deposit a part of the oxalic acid and/or niobium, whereby the concentration is preferably regulated.

Described hereinafter is an example of the method for preparing the mixed solution so that the niobium concentration is 0.3 to 1.0 mol/L at 10° C.

First, water is put in a mixing vessel. The water temperature is not limited but preferably 10 to 70° C. When a water temperature is below 10° C., the dissolution of the oxalic acid and niobic acid, which are the raw materials, does not proceed readily, whereas when a water temperature is higher than 70° C., the circumference of the inlet gets wet with steam and an accurate amount of niobium may not be added. The temperature for adding the niobic acid and the oxalic acid is not limited, and the niobium acid and the oxalic acid are preferably added at 70° C. or lower for the same reason as described above. The feeding order at this time is irrelevant. However, from the viewpoint of preventing the undissolution, it is preferred to add a niobic acid and an oxalic acid after water is fed. The feedstock oxalic acid/niobium molar ratio is 5.0 and the niobium concentration for the preparation is 0.520 (mol-Nb/kg-solution). When suspended, a small amount of ammonia water can be added.

The solution is heated to 80 to 95° C., however, it is preferable to raise the temperature in a rate of 1° C./hr since it takes longer time to reach the predetermined temperature and the decomposition of the oxalic acid is prevented from proceeding, and it is preferable to raise the temperature in a rate of 30° C./hr or less to prevent the oxalic acid from being decomposed when the temperature exceeds 95° C.

The aqueous mixed solution in which the oxalic acid and the Nb compound are dissolved is obtained by heating and stirring the solution at 80 to 95° C. The heating holding time is preferably 30 min. to 4 hours to reduce the undissolved niobium and, due to the decomposition of the oxalic acid, to prevent the redeposition of the niobium which has been dissolved in the complex formed with the oxalic acid. Subsequently, the aqueous mixed solution is cooled to 40° C. or lower and, at this time, the cooling rate is preferably 0.002 to 3° C./min. When a cooling rate is below 0.002° C./min., the niobium which has been dissolved in the complex formed with the oxalic acid may be redeposited due to the decomposition of the oxalic acid. On the other hand, when a cooling rate exceeds 3° C./min., the dissolved niobium complex is likely to be deposited as the temperature rapidly drops, failing to provide a uniform solution and reducing a niobium concentration in the solution, whereby the productivity may be reduced. When the aqueous solution is set to give an intended concentration at 10° C., it is preferred that the temperature of the aqueous mixed solution be adjusted to 30° C. or lower to deposit a part of the components and regulate the concentration. In this instance, after cooling the solution to 40° C. or lower, the temperature may be maintained at 30° C. for several hours to allow the excess oxalic acid to be deposited or may be lowered to about 1 to about 15° C. and maintained at that temperature. When the temperature is below 1° C., the water in the mixed solution is likely to freeze, causing the aqueous mixed solution to have uneven concentration. When the temperature exceeds 30° C., the oxalic acid is dissolved in an excess amount to give an oxalic acid concentration that is too high in the aqueous mixed solution, making it difficult to regulate a concentration to the intended concentration. To start the filtration after the oxalic acid is recrystallized, it is preferred that the solution be maintained for 30 minutes or more at a reduced temperature. However, when the solution is left to stand for 3 days or more, the crystal sticks in the mixing vessel and at the entrance of the pipe extending to the filter, likely causing the pipe to be blocked. In the preparation step of this aqueous mixed solution, the oxalic acid and niobium ratio can be regulated within the predetermined range depending on the temperature at which the solution is maintained.

The method for preparing the mixed solution of the present embodiment includes the step of feeding the aqueous mixed solution to a filter and filtering under increased pressure.

The filtration is carried out under increased pressure from the viewpoint of filtering efficiently and enhancing the productivity of the mixed solution. The pressure at this step is preferably 0.1 to 10 K/G in the light of the productivity efficiency and the pressure resistance properties of the filter paper.

Any filter paper insofar as it has the fineness of 5 species A or smaller can be used as necessary, and, for example, A No. 3250, manufactured by AZUMI FILTER PAPER CO., LTD., can be used. The thus obtained filtrate uniformly containing the dicarboxylic acid and niobium is extracted from the lower part of the container (X) which receives the filtrate. The extracted solution is stored in the storage container (Y) which is adjusted to the same temperature as that of the solution and used as a catalyst raw material. Further, it is preferred to provide a device capable of fractionating a part of the mixed solution while which is extracted. Furthermore, in the case of a ratio of dicarboxylic acid to niobium being not within the intended range, it is preferred to have the pot (Z) linked to the container (X) or the storage container (Y) via a pipe and to which the dicarboxylic acid and/or water can be added. To adjust the dicarboxylic acid/niobium ratio, a suitable amount of dicar- boxylic acid and/or water is fed to the pot (Z) and the dicarboxylic acid and/or water is dissolved in the mixed solution as the mixed solution is circulated between the pot (Z) and the container (Y) to control the ratio of the dicarboxylic acid and niobium. The dicarboxylic acid/Nb molar ratio (=X) of the filtrate (mixed solution) in this step is preferably adjusted to be 1<X<4. When X is 1 or less, the niobic acid, the raw material, may be deposited, whereas when X is 4 or more, the catalyst is over-reduced at the time of preparing the catalyst using the obtained mixed solution, particularly in the calcination step, whereby the catalyst performance is likely to be adversely affected.

In the filtration step, the aqueous mixed solution is preferably filtered while applying a pressure of 0.1 to 5 K/G to obtain a uniform solution. Further preferably, during the filtration, cool water is fed into a jacket provided outside the filter to maintain the temperature of the filtrate at 10 to 15° C. At this step, a uniform and clear mixed solution is obtained as the filtrate. When the dicarboxylic acid is an oxalic acid, the oxalic acid/niobium molar ratio of the mixed solution is analyzed as follows.

The mixed solution is dried over night in a crucible at 50 to 100° C., treated with heating at 300 to 800° C. for 1 to 10 hours, whereby the amount of solid Nb2O5 is determined. Based on this result, the concentration of niobium is calculated.

The concentration of the oxalic acid is calculated in accordance with the following method.

3 g of the mixed solution is precisely weighed and put in a 300 mL glass beaker, 200 mL of hot water at about 80° C. is added thereto, and 10 mL of a 1:1 sulfuric acid is then added thereto. The obtained mixed solution is titrated by using a ¼ N KMnO4 solution with stirring while being kept at a temperature of 70° C. on a hot stirrer. A point at which a faint light pink color by KMnO4 lasts for about 30 seconds or more is defined as an end-point. The concentration of the oxalic acid can be determined on the basis of the resultant titer in accordance with the following formula.

$$2KMnO_4+3H_2SO_4+5H_2C_2O_4 \rightarrow K_2SO_4+2MnSO_4+10CO_2+8H_2O$$

The obtained Nb mixed solution can be used, for example, as a niobium raw material in the preparation for oxide catalyst.

The method for preparing a catalyst of the present embodiment comprises preparing a mixed solution by the method described above and preparing a Mo, V, Sb and Nb-containing catalyst using the mixed solution.

Described below is an example in which the Nb mixed solution prepared by the above-described method is used in the preparation of an oxide catalyst containing niobium.

The raw materials other than the Nb raw material are not limited and, for example, the following compounds can be used. Examples of the Mo raw material include molybdenum oxide, ammonium dimolybdate, ammonium heptamolybdate, molybdophosphoric acid, silicomolybdic acid, with ammonium heptamolybdate being preferably used. Examples of the V raw material include vanadium pentoxide, ammonium metavanadate, vanadyl sulfate, with ammonium metavanadate being preferably used. An example of the preferably usable Sb raw material is an antimony oxide.

(Raw Material Preparation Step)

Hereinafter, an example of preparing a raw material prepared solution containing Mo, V, Nb and Sb is described more specifically.

First, ammonium heptamolybdate, ammonium metavanadate and antimony trioxide powder are added to water and heated to 80° C. or higher to prepare a mixed solution (B). At this time, for example, when the catalyst contains Ce, cerium nitrate can be added at the same time.

Next, in accordance with the intended composition, the Nb mixed solution (A) prepared earlier and the mixed solution (B) are mixed to obtain a raw material prepared solution. For example, when the catalyst contains W or Ce, a compound containing W is preferably mixed to obtain a raw material prepared solution. A preferably used example of the W containing compound is ammonium metatungstate. A preferably used example of the Ce containing compound is cerium nitrate hexahydrate. The W or Ce containing compound may be added to the mixed solution (B) or added at the same time of mixing the mixed solution (A) and the mixed solution (B). When the oxide catalyst is supported on a silica carrier, the raw material prepared solution is prepared so that the silica sol is contained, and, in this instance, the silica sol can be added as necessary.

When antimony is used, hydrogen peroxide is preferably added to the mixed solution (B) or to the solution containing the components of the mixed solution (B) in the process of the preparation. At this time H2O2/Sb (molar ratio) is preferably 0.01 to 5, more preferably 0.05 to 4. Further, at this time it is also preferable to keep stirring at 30 to 70° C. for 30 min to 2 hours. The thus obtained catalyst raw material prepared solution may sometimes be a uniform mixed solution but is typically a slurry.

(Drying Step)

In the drying step, the raw material prepared solution obtained in the above step is dried to obtain a dry powder. Drying can be carried out by known methods such as spray drying or evaporation to dryness, however, it is preferable to obtain micro spherical dry powder by the spray drying. Spraying in the spray drying method can be performed by a centrifugal system, a two-fluid-nozzle system, or a high-pressure nozzle system. Air heated by steam, and an electric heater or the like can be used as a heat source for drying. An inlet temperature of a dryer of a spray drying device is preferably 150 to 300° C., and an outlet temperature of the dryer is preferably 100 to 160° C.

(Calcining Step)

In the calcining step, the dry powder obtained in the drying step is calcined to obtain a composite oxide catalyst. A rotary kiln can be used as a calcining apparatus. The shape of a calcining device is not particularly limited, but when the shape of the calcining device is tubular, continuous calcination can be carried out, hence preferable. The shape of a calcining tube is not particularly limited but is preferably cylindrical. A heating system is preferably an external heating system and an electric furnace can appropriately be used. The size and material or the like of the calcining tube can be suitably selected according to calcining conditions and a production amount, but the inner diameter of the calcining tube is preferably 70 to 2000 mm, and more preferably 100 to 1200 mm. The length of the calcining tube is preferably 200 to 10000 mm, and more preferably 800 to 8000 mm. When an impact is imparted to the calcining device, the thickness of the calcining device is preferably 2 mm or more, and more preferably 4 mm or more, from the viewpoint that the calcining device has an enough thickness not to be broken by the impact. The thickness of the calcining device is preferably 100 mm or less, and more preferably 50 mm or less, from the viewpoint that the impact is sufficiently transmitted into the calcining device. The material of the calcining device is not particularly limited as long as it is heat resistant and has strength not to be broken by the impact, and SUS can be appropriately used.

A weir plate having a central part having a hole through which powder passes is provided vertically to the flow of the powder in the calcining tube, and thereby the calcining tube can be also partitioned into two or more zones. A holding time in the calcining tube is easily secured by disposing the weir plate. The number of the weir plates may be one or more. The material of the weir plate is preferably a metal, and a weir plate made of the same material as that of the calcining tube can appropriately be used. The height of the weir plate can be adjusted in accordance with a holding time which should be secured. For example, when powder is supplied at 250 g/hr using a rotary kiln having a calcining tube having an inner diameter of 150 mm and a length of 1150 mm and made of SUS, the height of the weir plate is preferably 5 to 50 mm, more preferably 10 to 40 mm, and still more preferably 13 to 35 mm. The thickness of the weir plate is not particularly limited, and is preferably adjusted in accordance with the size of the calcining tube. For example, when a rotary kiln has a calcining tube having an inner diameter of 150 mm and a length of 1150 mm and made of SUS, the thickness of the calcining tube is preferably 0.3 mm or more and 30 mm or less, and more preferably 0.5 mm or more and 15 mm or less.

In order to prevent crack and crazing or the like of the dry powder and to uniformly calcine the dry powder, the calcining tube is preferably rotated. The rotation speed of the calcining tube is preferably 0.1 to 30 rpm, more preferably 0.5 to 20 rpm, and still more preferably 1 to 10 rpm.

For the calcination of the dry powder, preferably, the heating temperature of the dry powder is continuously or intermittently raised to a temperature in the range of 550 to 800° C. from a temperature lower than 400° C.

A calcining atmosphere may be under an air atmosphere or under an air flow but at least a portion of the calcination is preferably carried out while an inert gas which does not substantially contain oxygen, such as nitrogen, flows. The supplied amount of the inert gas is 50 N liters or more per 1 kg of the dry powder, preferably 50 to 5000 N liters, and more preferably 50 to 3000 N liters (N liter means a liter measured under normal temperature and pressure conditions, that is, a litter measured at 0° C. and 1 atm). On this occasion, the flows of inert gas and the dry powder may be in the form of a counter flow or a parallel flow, but counter flow contact is preferable in consideration of gas components generated from the dry powder and a trace amount of air entering together with the dry powder.

The calcining step can be carried out in a single stage, but the calcination preferably includes pre-stage calcination and main calcination and the pre-stage calcination is carried out in the temperature range of 250 to 400° C. and main calcination is carried out in the temperature range of 550 to 800° C. The pre-stage calcination and the main calcination may be continuously carried out or the main calcination may be carried out anew once the pre-stage calcination has been completed. The pre-stage calcination and the main calcination may each be divided into several stages.

The pre-stage calcination is performed, preferably under an inert gas flow at a heating temperature of 250 to 400° C., and preferably 300 to 400° C. The pre-stage calcination is preferably held at a constant temperature within the temperature range of 250 to 400° C., but a temperature may fluctuate, or be gradually raised or lowered within the temperature range of 250 to 400° C. The holding time of the heating temperature is preferably 30 minutes or more, and more preferably 3 to 12 hours.

A temperature raising pattern until the pre-stage calcining temperature is reached may be linearly raised, or a temperature may be raised so that an arc of an upward or downward convex is formed.

A mean temperature raising rate during temperature raising until the pre-stage calcining temperature is reached is not particularly limited but the mean temperature raising rate is generally about 0.1 to about 15° C./min, preferably 0.5 to 5° C./min, and more preferably 1 to 2° C./min.

The main calcination is carried out, preferably under an inert gas flow, at 550 to 800° C., preferably at 580 to 750° C., more preferably at 600 to 720° C., and still more preferably at 620 to 700° C. The main calcination is preferably held at a constant temperature within the temperature range of 620 to 700° C. but a temperature may fluctuate, or be gradually raised or lowered within the temperature range of 620 to 700° C. The time of the main calcination is 0.5 to 20 hours, and preferably 1 to 15 hours. When the calcining tube is partitioned with a weir plate, the dry powder and/or a composite oxide catalyst continuously passes through at least 2 zones, preferably 2 to 20 zones, and more preferably 4 to 15 zones. A temperature can be controlled using one or more controllers but in order to obtain the desired calcining temperature pattern, a heater and a controller are preferably disposed in each of the zones partitioned with these weir plates to control the temperature. For example, when the seven weir plates are disposed so that a length of portion of the calcining tube entering a heating furnace is equally divided into eight, and the calcining tube partitioned into the eight zones is used, the setting temperature of each of the eight zones is preferably controlled by the heater and the controller disposed in each of the zones so that the temperature of the dry powder and/or the composite oxide catalyst has the desired calcining temperature pattern. An oxidizing component (for example, oxygen) or a reducing component (for example, ammonia) may be added to the calcining atmosphere under the inert gas flow as necessary.

A temperature raising pattern until the main calcining temperature is reached may be linearly raised, or a temperature may be raised so that an arc of an upward or downward convex is formed.

A mean temperature raising rate in temperature raising until the main calcining temperature is reached is not particularly limited, but is typically about 0.1 to 15° C./min, preferably 0.5 to 10° C./min, and more preferably 1 to 8° C./min.

A mean temperature lowering rate after the main calcination is completed is preferably 0.05 to 100° C./min, more preferably 0.1 to 50° C./min. A temperature lower than the main calcining temperature is also preferably held once. A holding temperature is lower than the main calcining temperature by 10° C., preferably 50° C., and more preferably 100° C. A holding time is 0.5 hours or more, preferably 1 hour or more, more preferably 3 hours or more, and still more preferably 10 hours or more.

When the main calcination is carried out anew once the pre-stage calcination has been completed, a low temperature treatment is preferably performed in the main calcination.

A time required for the low temperature treatment, that is, a time required for reducing the temperature of the dry powder and/or the composite oxide catalyst and raising the temperature to the calcining temperature can appropriately be adjusted by the size, the thickness, and the material of the calcining device, a catalyst production amount, a series of periods for continuously calcining the dry powder and/or the composite oxide catalyst, and a fixing rate and a fixing amount, or the like. For example, when a calcining tube having an inner diameter of 500 mm, a length of 4500 mm, and a thickness of 20 mm, and made of SUS is used, the time required for the low temperature treatment is preferably within 30 days during the series of periods for continuously calcining a catalyst, more preferably within 15 days, still more preferably within 3 days, and particularly preferably within 2 days.

For example, when the dry powder is supplied at a rate of 35 kg/hr while a rotary kiln having a calcining tube having an inner diameter of 500 mm, a length of 4500 mm, and a thickness of 20 mm and made of SUS is rotated at 6 rpm, and the main calcining temperature is set to 645° C., the step of lowering a temperature to 400° C. and raising the temperature to 645° C. can be performed in about 1 day. When the calcination is continuously performed for 1 year, the calcination can be performed by carrying out such low temperature treatment once a month while a temperature of an oxide layer is stably maintained.

Examples of the oxide catalyst obtained in the above step include the compound represented by the following general formula (1).

$$Mo_1V_aNb_bSb_cY_dO_n \tag{1}$$

wherein Y represents at least one element selected from Mn, W, B, Ti, Al, Te, alkali metals, alkali earth metals and rare earth metals, a, b, c, d and n each represent an atomic ratio of V, Nb, Sb and Y per Mo atom, with $0.1 \leq a \leq 1$, $0.01 \leq b \leq 1$, $0.01 \leq c \leq 1$ and $0 \leq d \leq 1$ and n represents the number of oxygen atom determined by the valence of a component element other than oxygen.

The atomic ratio a, b, c, d per Mo atom is each preferably $0.1 \leq a \leq 1$, $0.01 \leq b \leq 1$, $0.01 \leq c \leq 1$, $0 \leq d \leq 1$, more preferably $0.1 \leq a \leq 0.5$, $0.01 \leq b \leq 0.5$, $0.1 \leq c \leq 0.5$, $0.0001 \leq d \leq 0.5$, further preferably $0.2 \leq a \leq 0.3$, $0.05 \leq b \leq 0.2$, $0.2 \leq c \leq 0.3$, $0.0002 \leq d \leq 0.4$.

When the catalyst is used in a fluidized bed, a sufficient strength is required and the oxide catalyst is hence preferably carried on silica. The oxide catalyst is carried on, in terms of $SiO_2$, preferably 10 to 80 mass %, more preferably 20 to 60 mass %, further preferably 30 to 55 mass % of silica, with respect to the total mass of the oxide catalyst (the oxide of a catalyst composing element to be the principle catalyst) and the silica. From the viewpoint of strength and prevention of powdering, safe operation easily assured when a catalyst is used and reduction of the lost catalyst to be replenished, the content of silica is preferably 10 mass % or more based on the total amount of the oxide catalyst and the silica, whereas from the viewpoint of providing a sufficient catalyst activity, the content of silica is preferably 80 mass % or less with respect to the total amount of the oxide catalyst and the silica. In particular, when the catalyst is used in the fluidized bed, at a silica content of 80 mass % or less, the specific gravity of the silica carried catalyst (oxide catalyst+silica carrier) has a proper value, easily providing a good flow state.

[Method for Producing Unsaturated Nitrile]

The method for producing unsaturated nitrile of the present embodiment comprises preparing a catalyst by the method described above and allowing propane or isobutane, ammonia and oxygen to contact the obtained catalyst to produce unsaturated nitrile.

Using the oxide catalyst obtained by the production method of the present embodiment, propane or isobutane is allowed to react to ammonia and molecular oxygen in a vapor-phase (vapor-phase catalytic ammoxidation reaction), thereby producing a corresponding unsaturated nitrile (acrylonitrile or methacrylonitrile).

The feeding raw materials of propane or isobutane and ammonia do not necessarily have to be highly pure, and industrial-grade gases can be used. Air, pure oxygen or air enriched with pure oxygen can be used as a supply oxygen source. Further, as a dilution gas, helium, neon, argon, carbon dioxide, steam, and nitrogen or the like may be supplied.

When the ammoxidation reaction is carried out, a molar ratio of ammonia to be supplied for the reaction system to propane or isobutane is 0.3 to 1.5, preferably 0.8 to 1.2. For both oxidation reaction and ammoxidation reaction, a molar ratio of molecular oxygen to be supplied for the reaction system to propane or isobutane is 0.1 to 6, preferably 0.1 to 4.

For both oxidation reaction and ammoxidation reaction, the reaction pressure is 0.5 to 5 atm, and preferably 1 to 3 atm, the reaction temperature is 350 to 500° C., and preferably 380 to 470° C., and the contact time is 0.1 to 10 (sec·g/cc), and preferably 0.5 to 5 (sec·g/cc).

In the present embodiment, the contact time is defined by the following formula.

$$\text{Contact time (sec·g/cc)} = (W/F) \times 273/(273+T) \times P$$

wherein
W=Mass of catalyst (g),
F=Flow rate (Ncc/sec) of raw material mixed gas under normal conditions (0° C., 1 atm),
T=Reaction temperature (° C.),
P=Reaction pressure (atm)

The propane conversion rate and the yield of acrylonitrile respectively follow the following definitions.

Propane conversion rate (%)=(Number of moles of reacted propane)/(Number of moles of supplied propane)×100

Yield of Acrylonitrile (%)=(Number of moles of produced acrylonitrile)/(Number of moles of supplied propane)×100

As a reaction method, the conventional method such as a fixed bed method, a fluidized bed method, and a moving bed method can be used, but the fluidized bed reaction is preferable for reasons of easy removal of the reaction heat, the temperature of catalyst layer maintained approximately uniform, the catalyst that can be extracted from the reactor during the operation, the catalyst can be added, etc.

In the present embodiment, the yield (%) of niobium is defined by the following formula.

Yield=(water in the filtrate+niobium acid amount in the filtrate)/(feedstock water+niobium acid amount added)×100

In the present embodiment, the productivity (kg/min) is defined by the following formula.

Productivity=filtrate amount (kg)/time required to filter (min)

EXAMPLE

Hereinafter, the present embodiment will be further described in detail with reference to Examples and Comparative Examples but is not limited thereto.

In the following Examples and Comparative Examples, the apparatus for producing a mixed solution shown in FIG. 1 was used.

The material used for the mixing vessel is SUS316 and the mixing vessel used had the glass lined surface. The material for producing the pipe, filter, container, pot, and the like, was SUS316. The heating method for the mixing vessel was carried out by feeding steam into a jacket, and when cooling, the cooling was carried out by feeding cold water maintained at a constant temperature into the same jacket. For a stirring unit in the mixing vessel, stirring impellers were used.

Each evaluation was performed as follows.
(1) Yield of the Solution

Yield of the solution=(total weight of water and the niobic acid recovered in the container)/(total weight of feedstock water and the niobic acid)× 100

(2) Productivity

Productivity=(amount of the filtrate recovered in the container/time required for the filtration (min))× 100

(3) Anticorrosive Property (Corrosion Degree)

The anticorrosive property is a value, in mm/year, indicating how much a thickness (mm) of the mixing vessel is reduced after continuously used for one year based on the results of measuring the thickness (mm) of the mixing vessel after removing the rust therefrom after use as opposed to the thickness (mm) of the mixing vessel before use.

Example 1

500.0 kg of water was added to the mixing vessel and then the water was heated to 50° C. Then, with stirring, 270.0 kg of an oxalic acid dihydrate [$H_2C_2O_4.2H_2O$] was fed thereto, followed by feeding 72.2 kg of a niobic acid containing 78.9 mass % as Nb2O5 thereto, whereby both were mixed in water. The molar ratio of the feedstock oxalic acid/niobium was 5.0 and the concentration of feedstock niobium was 0.509 (mol-Nb/kg-solution).

The resultant solution was heated at 95° C. for 2 hours with stirring, thereby obtaining a uniform aqueous mixed solution. The pressure in the mixing vessel at this time was 1.2 K/G. The aqueous mixed solution was cooled in air with stirring to 40° C. and then allowed to stand for 12 hours while maintaining the temperature thereof at 35° C. Then, the aqueous mixed solution was cooled to 13° C. at a rate of −7.3° C./h and left standstill for 3 hours. When the aqueous mixed solution was cooled, the solid matter composed of the oxalic acid, the oxalic acid dihydrate, the niobium oxalate complex, etc., was deposited.

The pressure in the mixing vessel up to this step was always maintained at 1.2 K/G by feeding a compressed air during the cooling step, or the like. Subsequently, a mixture of the solid matter and the aqueous mixed solution was sent to the filter via the pipe and filtered to obtain a uniform mixed solution. The time required for the filtration was 60 minutes. The stirring was continued using a constant power until immediately before the solid matter and the aqueous mixed solution in the mixing vessel reached below the lower end of the stirring impellers (until the solution cannot be stirred). At this time, the filtration was carried out while applying a pressure of 0.7 K/G. The solution (the filtrate) was sampled respectively at 10 minutes, 60 minutes after the filtration started, measured for the temperature and found to have temperatures of 13° C., 15° C. The molar ratio of the oxalic acid/Nb on the mixed solution at each time was 2.79, 2.94 based on the following analysis, and the difference between the molar ratios of the oxalic acid/Nb at each time was 0.157. The color of the filtrate at this point was clear.

10 g of each of the mixed solution was precisely weighed and put in a crucible, dried over night at 95° C., and subjected to a heat treatment for one hour at 600° C., thereby obtaining 0.992, 0.970 g of the solid $Nb_2O_5$. From this result, the niobium concentrations were 0.589, 0.576 (mol-Nb/kg-solution).

3 g of each of the mixed solution was precisely weighed and put in a 300 mL glass beaker, 200 mL of hot water at about 80° C. was added thereto, and subsequently 10 mL of a 1:1 sulfuric acid was added thereto. The obtained mixed solution was titrated by using a ¼ N $KMnO_4$ solution with stirring while being kept at a temperature of 70° C. on a hot stirrer. A point at which a faint light pink color by KMnO4 lasts for about 30 seconds or more was defined as an end-point. The concentrations of the oxalic acid were determined on the basis of the resultant titers in accordance with the following formula, and found to be 1.64, 1.70 (mol-oxalic acid/kg). At this occasion, the yield of the solution was 97.7% and the productivity was 11.9 kg/min.

$2KMnO_4+3H_2SO_4+5H_2C_2O_4 \rightarrow K_2SO_4+2MnSO_4+ 10CO_2+8H_2O$

Example 2

1330.0 kg of water was added to the mixing vessel and then the water was heated to 50° C. Next, with stirring, 738.0 kg of an oxalic acid dihydrate [$H_2C_2O_4.2H_2O$] was fed thereto, followed by feeding 192.2 kg of a niobic acid containing 81.0 mass % as Nb2O5 thereto, whereby both were mixed in water. The molar ratio of the feedstock oxalic acid/niobium was 5.0 and the concentration of feedstock niobium was 0.518 (mol-Nb/kg-solution).

The resultant solution was heated at 95° C. for 2 hours with stirring, thereby obtaining a uniform aqueous mixed solution. The pressure in the mixing vessel then was 1.2 K/G. The aqueous mixed solution was cooled in air with stirring to 40° C. and then allowed to stand for 12 hours while maintaining the temperature thereof at 35° C. Then, the aqueous mixed solution was cooled to 13° C. at a rate of −7.3° C./h and left standstill for 3 hours. The pressure in the mixed solution vessel up to this step was always maintained at 1.2 K/G by feeding a compressed air during the cooling step, or the like. Subsequently, a mixture of the solid matter and the aqueous mixed solution was sent to the filter via the pipe and filtered to obtain a uniform mixed solution. The time required for the filtration was 130 minutes. The stirring was continued using a constant power until immediately before the solid matter and the aqueous mixed solution in the mixing vessel reached below the lower end of the stirring impellers. At this time, the filtration was carried out while applying a pressure of 0.5 K/G. The solution was sampled respectively at 10 minutes, 60 minutes and 120 minutes after the filtration started, measured for the temperature and found to have temperatures of 13° C., 18° C., 20° C. The molar ratio of the oxalic acid/Nb of the mixed solution at each time was 2.75, 2.89, 3.14 based on the following analysis, and the difference in the oxalic acid/Nb molar ratios between the filtrate sampled 120 minutes later and the filtrate sampled 10 minutes later was 0.394. The color of the filtrate at this point was clear.

10 g of each of the niobium raw material was precisely weighed and put in a crucible, dried over night at 95° C., and subjected to a heat treatment for one hour at 600° C., thereby obtaining 0.963, 0.941, 0.919 g of the solid $Nb_2O_5$. From this result, the niobium concentrations were 0.587, 0.573, 0.560 (mol-Nb/kg-solution).

3 g of each of the mixed solution was precisely weighed and put in a 300 mL glass beaker, 200 mL of hot water at about 80° C. was added thereto, and subsequently 10 mL of a 1:1 sulfuric acid was added thereto. The obtained mixed solution was titrated by using a ¼ N $KMnO_4$ solution with stirring while being kept at a temperature of 70° C. on a hot stirrer. A point at which a faint light pink color by $KMnO_4$ lasts for about 30 seconds or more was defined as an end-point. The oxalic acid concentrations were 1.61, 1.65, 1.76 (mol-oxalic acid/kg-solution). At this occasion, the yield of the solution was 96.8% and the productivity was 14.6 kg/min.

Example 3

500.0 kg of water was added to the mixing vessel and then the water was heated to 50° C. Next, with stirring, 298.2 kg of an oxalic acid dihydrate $[H_2C_2O_4.2H_2O]$ was fed thereto, followed by feeding 72.2 kg of a niobic acid containing 79.2 mass % as Nb2O5 thereto, whereby both were mixed in water. The molar ratio of the feedstock oxalic acid/niobium was 5.5 and the concentration of feedstock niobium was 0.494 (mol-Nb/kg-solution).

The resultant solution was heated at 95° C. for 2 hours with stirring, thereby obtaining a uniform aqueous mixed solution. The pressure in the mixing vessel then was 1.2 K/G. The aqueous mixed solution was cooled in air with stirring to 40° C. and then allowed to stand for 12 hours while maintaining the temperature thereof at 35° C. Then, the aqueous mixed solution was cooled to 12° C. at a rate of −7.3° C./h and left standstill for 3 hours. The pressure in the mixed solution vessel up to this step was always maintained at 1.2 K/G by feeding a compressed air during the cooling step, or the like. Subsequently, a mixture of the solid matter and the aqueous mixed solution was sent to the filter and filtered to obtain a uniform mixed solution. The time required for the filtration was 65 minutes. The stirring was continued using a constant power until immediately before the solid matter and the aqueous mixed solution in the mixing vessel reached below the lower end of the stirring impellers. At this time, the filtration was carried out while applying a pressure of 0.6 K/G. The temperature of the filter was then maintained at 12° C. by feeding cool water into the jacket disposed outside the filter. The solution was sampled at 10 minutes, 30 minutes, 60 minutes after the filtration started and measured for the temperature. The temperature of all solutions was 12° C., the molar ratio of the oxalic acid/Nb of the mixed solution at each time was 2.72, 2.70, 2.73 based on the following analysis, and the difference in the molar ratio of the oxalic acid/Nb at each time was 0.011. The color of the filtrate at this point was clear.

10 g of each of the niobium raw material was precisely weighed and put in a crucible, dried over night at 95° C., and subjected to a heat treatment for one hour at 600° C., thereby obtaining 1.006, 1.012, 1.014 g of the solid $Nb_2O_5$. From this result, the niobium concentrations were 0.599, 0.603, 0.604 (mol-Nb/kg-solution).

3 g of each of the mixed solution was precisely weighed and put in a 300 mL glass beaker, 200 mL of hot water at about 80° C. was added thereto, and subsequently 10 mL of a 1:1 sulfuric acid was added thereto. The obtained mixed solution was titrated by using a ¼ N $KMnO_4$ solution with stirring while being kept at a temperature of 70° C. on a hot stirrer. A point at which a faint light pink color by $KMnO_4$ lasts for about 30 seconds or more was defined as an end-point. From this result, the oxalic acid concentrations were 1.63, 1.63, 1.65 (mol-oxalic acid/kg). At this occasion, the yield of the solution was 97.2% and the productivity was 10.9 kg/min.

Example 4

Example 4 was carried out in the same manner as in Example 3 using an apparatus in a scale of ⅟500. 1.00 kg of water was added to the mixing vessel and then the water was heated to 50° C. Next, with stirring, 0.28 kg of an oxalic acid dihydrate $[H_2C_2O_4.2H_2O]$ was fed thereto, followed by feeding 0.14 kg of a niobic acid containing 78.9 mass % as $Nb_2O_5$ thereto, whereby both were mixed in water. The molar ratio of the feedstock oxalic acid/niobium was 5.0 and the concentration of feedstock niobium was 0.509 (mol-Nb/kg-solution).

The resultant solution was heated at 95° C. for 2 hours with stirring, thereby obtaining a uniform aqueous mixed solution. The pressure in the mixing vessel then was 1.2 K/G. The aqueous mixed solution was cooled in air with stirring to 40° C. and then allowed to stand for 12 hours while maintaining the temperature thereof at 35° C. Then, the aqueous mixed solution was cooled to 12° C. at a rate of −7.3° C./h and left standstill for 3 hours. The pressure in the mixed solution vessel up to this step was always maintained at 1.2 K/G by feeding a compressed air during the cooling step, or the like. Subsequently, a mixture of the solid matter and the aqueous mixed solution was sent to the filter and filtered by pressure filtration (pressure=0.7 K/G), thereby obtaining a uniform mixed solution. The time required for the filtration was 1 minutes. The stirring was continued using a constant power until immediately before the solid matter and the aqueous mixed solution in the mixing vessel reached below the lower end of the stirring impellers. The temperature of the filter was then maintained at 12° C. by feeding cool water into the jacket disposed outside the filter. The filtrate was sampled, measured for the temperature, and found to have a temperature of 12° C. The niobium concentration of the filtrate was 0.578 (mol-Nb/kg-solution) and the oxalic acid concentration was 1.59 (mol-oxalic acid/kg), based on which the molar ratio of the oxalic acid/Nb was 2.75. The color of the filtrate at this time was clear. Further, at this occasion, the yield of the solution was 97.5% and the productivity was 1.4 kg/min.

Example 5

500.0 kg of water was added to the mixing vessel and then the water was heated to 50° C. Next, with stirring, 107.7 kg of an oxalic acid dihydrate $[H_2C_2O_4.2H_2O]$ was fed thereto, followed by feeding 48.0 kg of a niobic acid containing 78.9 mass % as $Nb_2O_5$ thereto, whereby both were mixed in water. The molar ratio of the feedstock oxalic acid/niobium was 3 and the concentration of feedstock niobium was 0.435 (mol-Nb/kg-solution).

The resultant solution was heated at 95° C. for 2 hours with stirring, thereby obtaining a uniform aqueous mixed solution. The pressure in the mixing vessel then was 2.8 K/G. The aqueous mixed solution was cooled in air with stirring to 40° C. and then allowed to stand for 12 hours while maintaining the temperature thereof at 35° C. Then, the aqueous mixed solution was cooled to 8° C. at a rate of −7.3° C./h and left standstill for 3 hours. The pressure in the mixed solution vessel up to this step was always maintained at 2.8 K/G by feeding a compressed air during the cooling step, or the like. Subsequently, a mixture of the solid matter and the aqueous mixed solution was sent to the filter and filtered to obtain a uniform mixed solution. The time required for the filtration was 15 minutes. The stirring was continued using a constant power until immediately before the solid matter and the aqueous mixed solution in the mixing vessel reached below the lower end of the stirring impellers. At this time, the filtration was carried out while applying a pressure of 2.5 K/G. The temperature of the filter was then maintained at 8° C. by feeding cool water into the jacket disposed outside the filter. The solution was sampled at 15 minutes after the filtration started, measured for the temperature and found to have a temperature of 8° C., and the molar ratio of the oxalic acid/Nb of the mixed solution at this time was 2.01 based on the following analysis. The color of the filtrate at this point was clear.

10 g of each of the niobium raw material solutions was precisely weighed and put in a crucible, dried over night at 95° C., and subjected to a heat treatment for one hour at 600° C., thereby obtaining 0.762 g of the solid $Nb_2O_5$. From this result, the niobium concentration was 0.452 (mol-Nb/kg-solution).

3 g of each of the mixed solution was precisely weighed and put in a 300 mL glass beaker, 200 mL of hot water at about 80° C. was added thereto, and subsequently 10 mL of a 1:1 sulfuric acid was added thereto. The obtained mixed solution was titrated by using a ¼ N $KMnO_4$ solution with stirring while being kept at a temperature of 70° C. on a hot stirrer. A point at which a faint light pink color by $KMnO_4$ lasts for about 30 seconds or more was defined as an end-point. The oxalic acid concentration was 0.91 (mol-oxalic acid/kg). At this occasion, the yield of the solution was 97.6% and the productivity was 40.3 kg/min.

Example 6

500.0 kg of water was added to the mixing vessel and then the water was heated to 50° C. Then, with stirring, 224.4 kg of an oxalic acid dihydrate [$H_2C_2O_4.2H_2O$] was fed thereto, followed by feeding 100.0 kg of a niobic acid containing 78.9 mass % as $Nb_2O_5$ thereto, whereby both were mixed in water. The molar ratio of the feedstock oxalic acid/niobium was 3 and the concentration of feedstock niobium was 0.720 (mol-Nb/kg-solution).

The resultant solution was heated at 95° C. for 2 hours with stirring, thereby obtaining a uniform aqueous mixed solution. The pressure in the mixing vessel then was 2.8 K/G. The aqueous mixed solution was cooled in air with stirring to 40° C. and then allowed to stand for 12 hours while maintaining the temperature thereof at 35° C. Then, the aqueous mixed solution was cooled to 8° C. at a rate of −7.3° C./h and left standstill for 3 hours. The pressure in the mixed solution vessel up to this step was always maintained at 2.8 K/G by feeding a compressed air during the cooling step, or the like. Subsequently, a mixture of the solid matter and the aqueous mixed solution was sent to the filter and filtered to obtain a uniform mixed solution. The time required for the filtration was 30 minutes. The stirring was continued using a constant power until immediately before the solid matter and the aqueous mixed solution in the mixing vessel reached below the lower end of the stirring impellers. At this time, the filtration was carried out while applying a pressure of 2.5 K/G. The temperature of the filter was maintained at 8° C. by feeding cool water into the jacket disposed outside the filter. The solution was sampled at 10 minutes, 30 minutes, 60 minutes after the filtration started and measured for the temperature. The temperature of all solutions was 8° C., the molar ratio of the oxalic acid/Nb of the mixed solution at each time was 2.07, 2.09, 2.11 based on the following analysis, and the difference in the molar ratios of the oxalic acid/Nb at each time was 0.037. The color of the filtrate at this point was clear.

10 g of each of the niobium raw materials was precisely weighed and put in a crucible, dried over night at 95° C., and subjected to a heat treatment for one hour at 600° C., thereby obtaining 1.342, 1.332, 1.310 g of the solid $Nb_2O_5$. From this result, the niobium concentrations were 0.797, 0.790, 0.778 (mol-Nb/kg-solution).

3 g of each of the mixed solution was precisely weighed and put in a 300 mL glass beaker, 200 mL of hot water at about 80° C. was added thereto, and subsequently 10 mL of a 1:1 sulfuric acid was added thereto. The obtained mixed solution was titrated by using a ¼ N $KMnO_4$ solution with stirring while being kept at a temperature of 70° C. on a hot stirrer. A point at which a faint light pink color by $KMnO_4$ lasts for about 30 seconds or more was defined as an end-point. The oxalic acid concentrations were 1.65, 1.65, 1.64 (mol-oxalic acid/kg-solution). At this occasion, the yield of the solution was 95.8% and the productivity was 12.2 kg/min.

Comparative Example 1

A mixed solution was prepared in the same manner as in Example 4 with exception of using a mixing vessel with no glass lining, and the solution obtained was black. Further, the corrosion degree of the surface of the mixing vessel was measured and found to be 0.4 mm/year.

Comparative Example 2

500.0 kg of water was added to the mixing vessel and then the water was heated to 50° C. Then, with stirring, 270.0 kg of an oxalic acid dihydrate [$H_2C_2O_4.2H_2O$] was fed thereto, followed by feeding 72.2 kg of a niobic acid containing 78.9 mass % as $Nb_2O_5$ thereto, whereby both were mixed in water. The molar ratio of the feedstock oxalic acid/niobium was 5.0 and the concentration of feedstock niobium was 0.509 (mol-Nb/kg-solution).

The resultant solution was heated at 95° C. for 2 hours with stirring, thereby obtaining a uniform aqueous mixed solution. The pressure in the mixing vessel then was 1.2 K/G. The aqueous mixed solution was cooled in air with stirring to 40° C. and then allowed to stand for 12 hours while maintaining the temperature thereof at 35° C. Then, the aqueous mixed solution was cooled to 12° C. at a rate of −7.3° C./h and left standstill for 3 hours. The pressure in the mixed solution vessel up to this step was always maintained at 1.2 K/G by feeding a compressed air during the cooling step, or the like. Subsequently, a mixture of the solid matter and the aqueous mixed solution was sent to the filter and filtered by suction filtration (pressure=−0.2 K/G), thereby obtaining a uniform mixed solution. The time required for the filtration was 260 minutes. The stirring was continued using a constant power until immediately before the solid matter and the aqueous mix solution in the mixing vessel reached below the lower end of the stirring impellers. At this time, the temperature of the filter was not regulated. The solution was sampled at 10 minutes, 120 minutes, 240 minutes respectively after the filtration started, measured for the temperature and found to have temperatures of 12° C., 14° C., 15° C. and the niobium concentration at each time was 0.512, 0.575, 0.605 (mol-Nb/kg-solution). The oxalic acid concentrations were 1.41, 1.65, 1.86 (mol-oxalic acid/kg), and the molar ratios of the oxalic acid/Nb of the mixed solution were 2.75, 2.87, 3.08. The maximum concentration difference in the oxalic acid/Nb molar ratio at the sampling times was 0.330. The color of the filtrate at this point was clear. The yield of the solution was 82.7% and the productivity was 2.45 kg/min.

Comparative Example 3

500.0 kg of water was added to the mixing vessel and then the water was heated to 50° C. Then, with stirring, 270.0 kg of an oxalic acid dihydrate [$H_2C_2O_4.2H_2O$] was fed thereto, followed by feeding 72.2 kg of a niobic acid containing 78.9 mass % as $Nb_2O_5$ thereto, whereby both were mixed in water. The molar ratio of the feedstock oxalic acid/niobium was 5.0 and the concentration of feedstock niobium was 0.509 (mol-Nb/kg-solution).

The resultant solution was heated at 95° C. for 2 hours with stirring, thereby obtaining a uniform aqueous mix solution. The pressure in the mixing vessel then was 1.2 K/G. The aqueous mix solution was cooled in air with stirring to 40° C. and then allowed to stand for 12 hours while maintaining the temperature thereof at 35° C. Then, the aqueous mix solution was cooled to 10° C. at a rate of −7.3° C./h and left standstill for 3 hours. The pressure in the mixing vessel up to this step was always maintained at 1.2 K/G by feeding a compressed air during the cooling step, or the like. Subsequently, a mixture of the solid matter and the aqueous mixed solution was sent to the filter and filtered by suction filtration (pressure=−0.7 K/G), thereby obtaining a uniform mixed solution. The time required for the filtration was 70 minutes. The stirring was continued using a constant power until immediately before the solid matter and the aqueous mixed solution in the mixing vessel reached below the lower end of the stirring impellers. At this time, the temperature of the filter was not regulated. The filtrate was sampled at minutes, 60 minutes respectively after the filtration started, measured for the temperature and found to have temperatures of 10° C., 11° C. and the niobium concentrations at each time were 0.511, 0.547 (mol-Nb/kg-solution). The oxalic acid concentrations were 1.26, 1.48 (mol-oxalic acid/kg), and the molar ratios of the oxalic acid/Nb of the niobium raw material solution were 2.46, 2.70. Based on the above findings, the maximum concentration difference in the oxalic acid/Nb molar ratio at the sampling times was 0.244. The color of the filtrate at this point was clear. The yield of the solution was 78.8% and the productivity was 7.99 kg/min.

Comparative Example 4

500.0 kg of water was added to the mixing vessel and then the water was heated to 50° C. Then, with stirring, 270.0 kg of an oxalic acid dihydrate [$H_2C_2O_4.2H_2O$] was fed thereto, followed by stirring 72.2 kg of a niobic acid containing 78.9 mass % as $Nb_2O_5$ thereto, whereby both were mixed in water. The molar ratio of the feedstock oxalic acid/niobium was 5.0 and the concentration of feedstock niobium was 0.509 (mol-Nb/kg-solution).

The resultant solution was heated at 95° C. for 2 hours with stirring, thereby obtaining a uniform aqueous mixed solution. The pressure in the mixing vessel then was 1.2 K/G. The aqueous mixed solution was cooled in air to 40° C. and then allowed to stand for 12 hours while maintaining the temperature thereof at 35° C. Then, the aqueous mixed solution was cooled to 15° C. at a rate of −7.3° C./h and left standstill for 3 hours. The pressure in the mixing vessel up to this step was always maintained at 1.2 K/G by feeding a compressed air during the cooling step, or the like. Subsequently, a mixture of the solid matter and the aqueous mixed solution was sent to the filter and filtered by natural filtration, thereby obtaining a uniform mixed solution. The time required for the filtration was 750 minutes. The stirring was continued using a constant power until immediately before the solid matter and the aqueous mix solution in the mixing vessel reached below the lower end of the stirring impellers. At this time, the temperature of the filter was not regulated. The solution was sampled at 30 minutes, 360 minutes, 720 minutes respectively after the filtration started, measured for the temperature and found to have temperatures of 15° C., 19° C., 24° C. and the niobium concentrations at each time were 0.598, 0.581, 0.573 (mol-Nb/kg-solution). The oxalic acid concentrations were 1.72, 1.86, 1.98 (mol-oxalic acid/kg), and the molar ratios of the oxalic acid/Nb of the niobium raw material solutions were 2.88, 3.20, 3.45. Based on the above findings, the maximum concentration difference in the oxalic acid/Nb molar ratio at the sampling times was 0.571. The color of the filtrate at this point was clear. The yield of the solution was 84.2% and the productivity was 0.86 kg/min.

Comparative Example 5

500.0 kg of water was added to the mixing vessel and then the water was heated to 50° C. Then, with stirring, 270.0 kg of an oxalic acid dihydrate [$H_2C_2O_4.2H_2O$] was fed thereto, followed by feeding 72.2 kg of a niobic acid containing 78.9 mass % as $Nb_2O_5$ thereto, whereby both were mixed in water. The molar ratio of the feedstock oxalic acid/niobium was 5.0 and the concentration of feedstock niobium was 0.509 (mol-Nb/kg-solution).

The resultant solution was heated at 95° C. for 2 hours with stirring, thereby obtaining a uniform aqueous mixed solution. The pressure in the mixing vessel then was 1.2 K/G. The aqueous mixed solution was cooled in air to 40° C. and then allowed to stand for 12 hours while maintaining the temperature thereof at 35° C. Then, the aqueous mixed solution was cooled to 10° C. at a rate of −7.3° C./h and left standstill for 3 hours. The pressure in the mixed solution vessel up to this step was always maintained at 1.2 K/G by feeding a compressed air during the cooling step, or the like. Subsequently, a mixture of the solid matter and the aqueous mixed solution was sent to the filter and filtered by natural filtration, thereby obtaining a uniform mixed solution. The time required for the filtration was 780 minutes. The stirring was continued using a constant power until immediately before the solid matter and the aqueous mixed solution in the mixing vessel reached below the lower end of the stirring impellers. At this time, the filtration was carried out by adjusting the temperature of the filter to 15° C. by feeding cool water into the jacket. The filtrate was sampled at 10 minutes, 720 minutes respectively after the filtration started, measured for the solution temperature and found to have temperatures of 15° C., 15° C. and the niobium concentrations at each time were 0.640, 0.638 (mol-Nb/kg-solution). The oxalic acid concentrations were 1.80, 1.82 (mol-oxalic acid/kg), and the molar ratios of the oxalic acid/Nb of the niobium raw material solutions were 2.81, 2.85. Based on the above findings, the maximum concentration difference in the oxalic acid/Nb molar ratio at the sampling times was 0.039. The color of the filtrate at this point was clear. The yield of the solution was 85.3% and the productivity was 0.81 kg/min.

Comparative Example 6

A mixed solution was prepared using the same apparatus as in Example 4.

1.00 kg of water was added to the mixing vessel and then the water was heated to 50° C. Then, with stirring, 0.28 kg of an oxalic acid dihydrate [$H_2C_2O_4.2H_2O$] was fed thereto, followed by feeding 0.14 kg of a niobic acid containing 82.0 mass % as $Nb_2O_5$ thereto, whereby both were mixed in water. The molar ratio of the feedstock oxalic acid/niobium was 5.0 and the concentration of feedstock niobium was 0.522 (mol-Nb/kg-solution).

The resultant solution was heated at 95° C. for 2 hours with stirring, thereby obtaining a uniform aqueous mix solution. The pressure in the mixing vessel then was 1.2 K/G. The aqueous mixed solution was cooled in air to 40° C. and then allowed to stand for 12 hours while maintaining the temperature thereof at 35° C. Then, the aqueous mix solution was cooled to 16° C. at a rate of −7.3° C./h and left standstill for 3 hours. The pressure in the mixed solution vessel up to this step was always maintained at 1.2 K/G by feeding a compressed air during the cooling step, or the like. Subsequently, a mixture of the solid matter and the aqueous mixed solution was sent to the filter and filtered by suction filtration (pressure=−0.7 K/G), thereby obtaining a uniform mixed solution. The time required for the filtration was 25 minutes. The stirring was continued using a constant power until immediately before the solid matter and the aqueous mix solution in the mixing vessel reached below the lower end of the stirring impellers. At this time, the filtration was carried out without regulating the temperature of the filter. The filtrate was sampled at 10 minutes, 20 minutes respectively after the filtration started, measured for the temperature and found to have temperatures of 16° C., 18° C. and the niobium concentrations at each time were 0.593, 0.602 (mol-Nb/kg-solution). The oxalic acid concentrations were 1.63, 1.73 (mol-oxalic acid/kg), and the molar ratios of the oxalic acid/Nb of the niobium raw material solutions were 2.75, 2.88. Based on the above findings, the maximum concentration difference in the oxalic acid/Nb molar ratio at the sampling times was 0.132. The color of the filtrate at this point was clear. At this occasion, the yield of the solution was 93.8% and the productivity was 0.06 kg/min.

Comparative Example 7

500.0 kg of water was added to the mixing vessel and then the water was heated to 50° C. Then, with stirring, 270.0 kg of an oxalic acid dihydrate [$H_2C_2O_4.2H_2O$] was fed thereto, followed by feeding 72.2 kg of a niobic acid containing 78.9 mass % as $Nb_2O_5$ thereto, whereby both were mixed in water. The molar ratio of the feedstock oxalic acid/niobium was 5.0 and the concentration of feedstock niobium was 0.509 (mol-Nb/kg-solution).

The resultant solution was heated at 95° C. for 2 hours with stirring, thereby obtaining a uniform aqueous mix solution. The pressure in the mixing vessel then was 1.2 K/G. The aqueous mixed solution was cooled in air to 40° C. and then allowed to stand for 12 hours while maintaining the temperature thereof at 35° C. Then, the aqueous mixed solution was cooled to 15° C. at a rate of −7.3° C./h and left standstill for 3 hours. The pressure in the mixed solution vessel up to this step was always maintained at 1.2 K/G by feeding a compressed air during the cooling step, or the like. Subsequently, a mixture of the solid matter and the aqueous mixed solution was sent to the filter and filtered by suction filtration (pressure=−0.7 K/G), thereby obtaining a uniform mixed solution. The time required for the filtration was 65 minutes. The stirring was continued using a constant power until immediately before the solid matter and the aqueous mixed solution in the mixing vessel reached below the lower end of the stirring impellers. At this time, the filtration was carried out by adjusting the temperature of the filter to 15° C. by feeding cool water into the jacket. The filtrate was sampled at 10 minutes, 60 minutes respectively after the filtration started, measured for the solution temperature and found to have the same temperature of 15° C., and the niobium concentrations at each time were 0.589, 0.685 (mol-Nb/kg-solution). The oxalic acid concentrations were 1.74, 2.05 (mol-oxalic acid/kg), and the molar ratios of the oxalic acid/Nb of the niobium raw material solutions were 2.96, 3.00. Based on the above findings, the maximum concentration difference in the oxalic acid/Nb molar ratio at the sampling times was 0.038. The color of the filtrate at this point was clear. The yield of the solution was 78.6% and the productivity was 9.3 kg/min.

Table 1 below shows the results of each of Examples and Comparative Examples.

TABLE 1

| | Feedstock | Claim 1 | | Claim 2 Filter | Effect | | | |
|---|---|---|---|---|---|---|---|---|
| | water scale (kg) | Mixing vessel (anticorrosiveness) | Filtration method | temperature adjustment | Yield (%) | ΔOx/Nb ratio | Anticorrosiveness (mm/year) | Productivity (kg/min) |
| Ex. 1 | 500 Kg | Yes | Applied pressure | No | 97.7 | 0.157 | 0.0 | 11.9 |
| Ex. 2 | 1000 Kg | Yes | Applied pressure | No | 96.8 | 0.394 | 0.0 | 14.6 |
| Ex. 3 | 500 Kg | Yes | Applied pressure | Yes | 97.2 | 0.011 | 0.0 | 10.9 |
| Ex. 4 | 1 Kg | Yes | Applied pressure | Yes | 97.5 | 0.000 | 0.0 | 1.4 |
| Ex. 5 | 500 Kg | Yes | Applied pressure | Yes | 97.6 | 0.000 | 0.0 | 40.3 |
| Ex. 6 | 500 Kg | Yes | Applied pressure | Yes | 95.8 | 0.037 | 0.0 | 12.2 |
| Comp. Ex. 1 | 1 Kg | No | Applied pressure | No | 97.3 | 0.000 | 0.4 | 1.4 |
| Comp. Ex. 2 | 500 Kg | Yes | Reduced pressure | No | 82.7 | 0.330 | 0.0 | 2.5 |

TABLE 1-continued

|  | Feedstock | Claim 1 | | Claim 2 Filter | Effect | | | |
|---|---|---|---|---|---|---|---|---|
|  | water scale (kg) | Mixing vessel (anticorrosiveness) | Filtration method | temperature adjustment | Yield (%) | ΔOx/Nb ratio | Anticorrosiveness (mm/year) | Productivity (kg/min) |
| Comp. Ex. 3 | 500 Kg | Yes | Reduced pressure | No | 78.8 | 0.244 | 0.0 | 8.0 |
| Comp. Ex. 4 | 500 Kg | Yes | Natural | No | 84.2 | 0.571 | 0.0 | 0.9 |
| Comp. Ex. 5 | 500 Kg | Yes | Natural | Yes | 85.3 | 0.039 | 0.0 | 0.81 |
| Comp. Ex. 6 | 1 Kg | Yes | Reduced pressure | No | 93.8 | 0.132 | 0.0 | 0.06 |
| Comp. Ex. 7 | 500 Kg | Yes | Reduced pressure | Yes | 78.6 | 0.038 | 0.0 | 9.3 |

In the Table, "ΔOxalic acid/Nb ratio" refers to the concentration difference in the oxalic acid/Nb ratio between the oxalic acid/Nb ratio measured at the first sampling and the oxalic acid/Nb ratio measured at the last sampling during the filtration time. However, the oxalic acid/Nb ratio was not measured when the filtration time was within 20 minutes.

Example 6

Described below is an example of preparing a composite oxide catalyst using the mixed solution prepared in Example 1.
(Preparation of Dry Powder)

30.24 kg of ammonium heptamolybdate [(NH$_4$)$_6$Mo$_7$O$_{24}$.4H$_2$O], 4.19 kg of ammonium metavanadate [NH$_4$VO$_3$], 5.52 kg of antimony trioxide [Sb$_2$O$_3$] and further 371 g of cerium nitrate [Ce(NO$_3$)$_3$.6H$_2$O] dissolved in advance in 26 kg of water were added to 100 kg of water and heated at 95° C. for 1 hour with stirring, thereby obtaining an aqueous mixed solution A-1.

To 29.9 kg of the mixed solution prepared in Example 1, 3.42 kg of hydrogen peroxide solution containing 30 mass % on an H$_2$O$_2$ basis was added. The solution was maintained at about 20° C. and mixed with stirring, thereby obtaining an aqueous solution B-1.

After cooling the obtained aqueous mixed solution A-1 to 70° C., 56.55 kg of silica sol containing 32.0 mass % on an SiO$_2$ basis was added thereto. Subsequently, 6.44 kg of hydrogen peroxide solution containing 30 mass % on an H$_2$O$_2$ basis was added thereto, mixed with stirring at 50° C. for 1 hour, and 2.38 kg of an aqueous solution of ammonium metatungstate was dissolved therein, thereby obtaining an aqueous solution B-1. Further, a raw material prepared solution to which a solution wherein 14.81 kg of fumed silica was dispersed in 214.7 kg of water was added was aged with stirring at 50° C. for 2.5 hours, thereby obtaining a slurry aqueous mixed solution (C1).

The obtained aqueous mixed solution (C1) was fed to a centrifugal spray dryer and dried, thereby obtaining a microspherical dry powder. The temperature at the inlet of the dryer was 210° C. and the temperature at the outlet thereof was 120° C. This step was repeated 38 times and prepared a total of about 2600 kg of the dry power (D1).
(Classification Operation)

The obtained dry powder (D1) was classified using a sieve having a 25 μm mesh to obtain the classified product (E1). The obtained classified product (E1) had a 0.8 wt. % content of the particle having 25 μm or less and the average particle diameter of 55 μm.

(Calcination of Classified Product (E1))

The obtained classified product (E1) is fed at a rate of 20 kg/hr into an SUS cylindrical calcining tube, having an inner diameter of 500 mm, a length of 3500 mm and a thickness of 20 mm with 7 weir plates having a length of 150 mm disposed so that a length of the heating furnace portion is equally divided into eight, and subjected to the pre-stage calcination while the calcining tube is rotated 4 times/min under a stream of nitrogen gas in 600 NL/min and the temperature of the heating furnace is adjusted to have the temperature profile wherein the temperature was raised to 370° C. over about 4 hours and maintained at 370° C. for 3 hours, thereby obtaining a pre-stage calcined product. The pre-stage calcined product was fed at a rate of 15 kg/hr into another SUS cylindrical calcining tube, having an inner diameter of 500 mm, a length of 3500 mm and a thickness of 20 mm with 7 weir plates having a length of 150 mm disposed so that a length of the heating furnace portion is equally divided into eight while the calcining tube was rotated 4 times/min. Then, the main calcination was carried out while the powder feeding side (the part not covered by the heating furnace) of the calcining tube was hit once every 5 seconds, using a hammering device equipped with a hammer having a mass of 14 kg and the hitting member with the SUS tip, from a height of 250 mm above the upper part of the calcining tube in a perpendicular direction to the rotating shaft and the temperature of the heating furnace is adjusted to have the temperature profile wherein the temperature was raised to 680° C. at 2° C./min under a stream of nitrogen gas in 500 NL/min, maintained at 680° C. for calcination for 2 hours and reduced at 1° C./min, thereby obtaining an oxide catalyst.

Example 7

Described below is an example of preparing acrylonitrile using the oxide catalyst prepared in Example 6.
(Ammoxidation Reaction of Propane)

40 g of the composite oxide catalyst obtained in the above was loaded in a glass fluidized bed reactor having an inner diameter of 1B, a mixed gas having a molar ratio of propane:ammonia:oxygen:helium=1:1:3:18 was supplied thereto in a contact time of 2.9 (sec·g/cc) at a reaction temperature of 440° C. under a normal reaction pressure to carry out an ammoxidation reaction for 10 days, thereby finding the average yield of acrylonitrile to be 55%.

The present invention is based on a Japanese patent application (Japanese Patent Application No. 2011-017937)

filed on Jan. 31, 2011 with Japan Patent Office, and the disclosure of which is herein incorporated by reference.

INDUSTRIAL APPLICABILITY

The mixed solution obtained by using the apparatus for producing a mixed solution according to the present invention has potential to be industrially applicable as a raw material for preparing the catalyst for the production of unsaturated nitrile.

The invention claimed is:

1. A method for preparing a mixed solution, comprising the steps of:
    heating and stirring a dicarboxylic acid, a niobium compound and water in an anticorrosive mixing vessel so as to obtain an aqueous mixed solution;
    cooling and stirring the aqueous mixed solution; and
    feeding the aqueous mixed solution into a filter to filter under an increased pressure.

2. The method for preparing the mixed solution according to claim 1, wherein a temperature of the aqueous mixed solution is adjusted in the step of feeding the aqueous mixed solution into a filter.

3. The method for preparing the mixed solution according to claim 1, wherein in the step of heating and stirring the dicarboxylic acid, the niobium compound and the water in an anticorrosive mixing vessel to obtain the aqueous mixed solution, a niobium and a dicarboxylic acid are dissolved in the aqueous mixed solution.

4. The method for preparing the mixed solution according to claim 1, wherein in the step of cooling and stirring the aqueous mixed solution, the dicarboxylic acid is deposited from the aqueous mixed solution.

5. The method for preparing the mixed solution according to claim 1, further comprising the steps of:
    measuring a concentration of an obtained filtrate after the step of feeding the aqueous mixed solution into a filter and
    adding a dicarboxylic acid and/or water to the filtrate when a dicarboxylic acid/niobium molar ratio is not within a predetermined range.

6. The method for preparing the mixed solution according to claim 5, wherein a molar ratio of the dicarboxylic acid to the niobium of the filtrate is adjusted to more than 1 and less than 4.

7. The method for preparing the mixed solution according to claim 1, wherein the dicarboxylic acid is an oxalic acid.

8. A method for preparing a molybdenum, vanadium, antimony and niobium-containing catalyst comprising:
    preparing a mixed solution according to claim 1 and;
    mixing together the mixed solution and a solution comprising molybdenum, vanadium and antimony.

9. A method for producing an unsaturated nitrile, comprising:
    preparing a catalyst by the method according to claim 8; and
    contacting the catalyst with i) propane, ammonia and oxygen or ii) isobutane, ammonia and oxygen, so as to produce the unsaturated nitrile.

* * * * *